US011524096B2

(12) United States Patent
McBurney et al.

(10) Patent No.: US 11,524,096 B2
(45) Date of Patent: Dec. 13, 2022

(54) WETTING AGENT FORMULATION

(71) Applicant: TELEFLEX LIFE SCIENCES PTE. LTD., Singapore (SG)

(72) Inventors: Denzell McBurney, Castledaly Moate County (IE); Ronald John Kelly, Oranmore County (IE); Morgan Tierney, Tullamore County (IE)

(73) Assignee: TELEFLEX LIFE SCIENCES PTE. LTD., Singapore (SG)

( * ) Notice: Subject to any disclaimer, the term of this patent is extended or adjusted under 35 U.S.C. 154(b) by 103 days.

(21) Appl. No.: 16/324,437

(22) PCT Filed: Aug. 9, 2017

(86) PCT No.: PCT/EP2017/000970
§ 371 (c)(1),
(2) Date: Feb. 8, 2019

(87) PCT Pub. No.: WO2018/028831
PCT Pub. Date: Feb. 15, 2018

(65) Prior Publication Data
US 2019/0167849 A1    Jun. 6, 2019

(30) Foreign Application Priority Data

Aug. 9, 2016  (EP) .................................... 16001766

(51) Int. Cl.
| | |
|---|---|
| *A61L 29/00* | (2006.01) |
| *A61L 29/08* | (2006.01) |
| *A61L 27/34* | (2006.01) |
| *A61L 29/14* | (2006.01) |
| *A61L 27/52* | (2006.01) |
| *A61L 27/50* | (2006.01) |
| *A61K 39/00* | (2006.01) |
| *C08L 1/28* | (2006.01) |
| *A61L 2/08* | (2006.01) |
| *A61M 25/00* | (2006.01) |
| *B65B 55/16* | (2006.01) |
| *A61L 2/10* | (2006.01) |
| *C08J 3/03* | (2006.01) |
| *C08K 5/06* | (2006.01) |
| *C08K 5/134* | (2006.01) |

(52) U.S. Cl.
CPC ........ *A61L 29/085* (2013.01); *A61K 39/0002* (2013.01); *A61L 2/081* (2013.01); *A61L 27/34* (2013.01); *A61L 27/50* (2013.01); *A61L 27/505* (2013.01); *A61L 27/52* (2013.01); *A61L 29/08* (2013.01); *A61L 29/14* (2013.01); *A61L 29/143* (2013.01); *A61L 29/145* (2013.01); *A61M 25/002* (2013.01); *B65B 55/16* (2013.01); *C08L 1/286* (2013.01); *A61L 2/10* (2013.01); *A61L 2202/18* (2013.01); *A61L 2202/24* (2013.01); *A61L 2400/10* (2013.01); *A61L 2420/02* (2013.01); *C08J 3/03* (2013.01); *C08K 5/06* (2013.01); *C08K 5/1345* (2013.01)

(58) Field of Classification Search
None
See application file for complete search history.

(56) References Cited

U.S. PATENT DOCUMENTS

| | | | |
|---|---|---|---|
| 3,634,078 A * | 1/1972 | Uhlig | ........................ B41N 3/03 430/60 |
| 3,894,540 A | 7/1975 | Bonner, Jr. | |
| 5,501,105 A * | 3/1996 | Hernandez | ............. G01H 1/003 324/226 |
| 6,299,905 B1 | 10/2001 | Peterson et al. | |
| 6,733,787 B2 | 5/2004 | Peterson et al. | |
| 6,923,985 B2 | 8/2005 | Peterson et al. | |
| 7,122,205 B2 | 10/2006 | Peterson et al. | |
| 8,147,769 B1 * | 4/2012 | Huang | .................... A61L 31/16 422/243 |
| 8,747,882 B2 | 6/2014 | Utas et al. | |

(Continued)

FOREIGN PATENT DOCUMENTS

| | | |
|---|---|---|
| CA | 2837045 A1 | 11/2012 |
| WO | 98/19729 A1 | 5/1998 |

(Continued)

OTHER PUBLICATIONS

Arunkumar et al, Synthesis, Characterisation and BiologicalEvaluation of some novel 2,5-Disubstituted-1,3,4-oxadiazole derivatives of Gallic acid, international journal of chemtech research, 1, 4, 1094-1099 (Year: 2009).*

Huynh Nguyen, et al., Sterilization of allograft bone: Is 25 k Gy the gold standard for gamma irradiation?, Cell Tissue Banking, 2007, pp. 81-91, vol. 8.

* cited by examiner

*Primary Examiner* — Stefanie J Cohen
(74) *Attorney, Agent, or Firm* — BakerHostetler

(57) ABSTRACT

A first alternative to a composition for preventing or retarding degradation of a functional coating on a medical device includes an antioxidant selected from gallic acid or a derivative thereof. A second alternative to a composition for preventing or retarding degradation of a functional coating on a medical device includes carboxymethyl cellulose or a derivative or salt thereof. The use of the compositions for preventing or retarding degradation of a functional coating on a medical device from reactive species generated during exposure of radiation, and a wetting agent comprising the compositions, are also provided. The wetting agent prevents or retards the hydrolytic degradation of the coating during the intended shelf-life of the wetted coated product.

10 Claims, No Drawings

(56) References Cited

U.S. PATENT DOCUMENTS

| | | | | |
|---|---|---|---|---|
| 2002/0026882 A1* | 3/2002 | Patel | ............... | C09D 5/008 |
| | | | | 106/14.11 |
| 2010/0209472 A1* | 8/2010 | Wang | ............... | A61L 31/16 |
| | | | | 424/423 |

FOREIGN PATENT DOCUMENTS

| | | | |
|---|---|---|---|
| WO | 00/30696 | A1 | 6/2000 |
| WO | 00/47494 | A1 | 8/2000 |
| WO | 2006/037321 | A1 | 4/2006 |
| WO | 2006/117372 | A1 | 11/2006 |
| WO | 2007/065721 | A2 | 6/2007 |
| WO | 2007/065722 | A1 | 6/2007 |
| WO | 2007/137699 | A1 | 12/2007 |
| WO | 2008/151074 | A1 | 12/2008 |
| WO | 2010/003419 | A2 | 1/2010 |
| WO | 2011/076217 | A1 | 6/2011 |
| WO | 2012/085107 | A2 | 6/2012 |
| WO | 2013/017547 | A1 | 2/2013 |
| WO | 2013/053809 | A1 | 4/2013 |
| WO | 2014/116812 | A2 | 7/2014 |

WETTING AGENT FORMULATION

CROSS-REFERENCE TO RELATED APPLICATIONS

This application is a National Stage of International patent application PCT/EP2017/000970, filed on Aug. 9, 2017, which claims priority to foreign European patent application No. EP 16001766.1, filed on Aug. 9, 2016, the disclosures of which are incorporated by reference in their entirety.

FIELD OF THE INVENTION

The present invention relates to a composition for preventing or retarding degradation of a functional coating on a medical device, the use of the composition, and a wetting agent comprising the composition.

It is well-known to coat medical devices with a lubricant to the outer surface, in particular to facilitate insertion into or removal from the body, e.g. blood vessels, digestive organs and the urinary system. Such lubricious properties are also desired to minimize tissue damage during insertion or removal. Usually, medical devices may be provided with a hydrophilic coating on which a wetting fluid is applied. The wetting fluid protects the coating from drying out and thereby maintains the lubricious properties of the coating. Examples of wetting fluids are water, mixtures of water and organic solvents, a body fluid, and aqueous solutions of salts, e.g. a saline solution having physiological osmolarity.

Medical devices can be wetted immediately prior to use or can be stored in the wetting liquid. In particular, it is desirable to provide a ready-to-use medical device, wherein the medical device with a hydrophilic coating is in a sterile package that contains enough wetting liquid to keep the coating wetted and thereby lubricious.

Suitable sterilization techniques for medical devices are well-known to the skilled person, such as autoclaving or irradiation. During sterilization, reactive intermediates can be formed, which may attack the hydrophilic coating of the medical device. Furthermore, most hydrophilic coatings lose their water retention and lubricious properties when the coatings are stored for an extended period of time and/or after sterilization using autoclaving or irradiation.

WO-A-00/30696 describes a method for sterilizing a medical device comprising a hydrophilic coating by irradiation. It was found that the water retention can be increased and the coefficient of friction can be kept low by adding hydrophilic polymers to the wetting liquid.

WO-A-2007/137699 discloses the use of a compound selected from aliphatic compounds, alicyclic compounds and antioxidants for protecting a hydrophilic coating which is sterilized by irradiation, in particular γ-radiation or Electron-beam (E-beam) radiation. discloses the use of a compound selected from aliphatic compounds, alicyclic compounds and antioxidants for protecting a hydrophilic coating which is sterilized by irradiation, in particular γ-radiation or Electron-beam (E-beam) radiation.

WO-A-2013/017547 is directed to the use of a wetting liquid, which may comprise water in an amount of 0 to 4.9 wt % and has a boiling point higher than 100° C. and a viscosity lower than 500 mPaxs.

WO-A-2006/037321 is directed to a medical device having a wetted hydrophilic coating and which is in a ready-to-use form. The wetted hydrophilic coating comprises a coating composition comprising a hydrophilic polymer and a wetting agent comprising water and one or more lubricants.

WO-A-2006/117372 describes sterilization of medical devices having a wetted hydrophilic coating using radiation. It was found that when adding hydrophilic polymers to the storage medium prior to sterilization a high water retention and a low friction is maintained when the medical device is stored in water.

WO-A-2011/076217 discloses a medical device having a hydrophilic coating and being sterilized while in contact with a swelling medium comprising a low molecular polyol and a separate buffer. The pH is in the range of from 4 to 7.4. Furthermore, ascorbic acid may be added as a stabilizing agent, but that depends on the substrate, type of hydrophilic coating and gamma irradiation dosage.

WO-A-2010/003419 relates to a medical device having a hydrophilic coating and being sterilized while in contact with a liquid comprising a hydrophilic polymer and a separate buffer.

WO-A-2012/085107 is directed to a hydrophilic catheter assembly including a wetting fluid.

The wetting fluid is preferably an aqueous liquid, such as sterile water or saline.

WO-A-2008/151074 discloses a lubricant for medical devices which is suitable for radiation sterilization.

WO-A-00/47494 relates to a storage package which contains a medical device having a coated surface which exhibits a reduced friction when wetted.

WO-A-2007/065721 and WO-A-2007/065722 describe a hydrophilic coating composition which when cured results in a hydrophilic coating. It was found that a lubricious coating with a prolonged and improved dry-out time may be obtained when a polyelectrolyte is included in the hydrophilic coating from which said lubricious coating ins formed by applying a wetting fluid.

However, the compositions of the above-cited prior art are highly specific and can be used only for a limited group of hydrophilic coatings. Furthermore, the particular components present in the composition have to be selected depending on the hydrophilic coating or the base solution.

The object of the present invention is to provide a composition which overcomes the disadvantages of the prior art and which is able to prevent or retard degradation of a functional coating on a medical device, which has improved properties, in particular is non-toxic, easy to prepare, radiation sterilizable, cheap and cost effective, and can be used for a large variety of functional coatings.

This object is achieved by a composition for preventing or retarding degradation of a functional coating on a medical device comprising an antioxidant selected from gallic acid or a derivative thereof.

This object is also achieved by a composition for preventing or retarding degradation of a functional coating on a medical device comprising carboxymethyl cellulose or a derivative or salt thereof.

The object is further achieved by the use of the composition for preventing or retarding degradation of a functional coating on a medical device from reactive species generated during exposure of radiation and/or from hydrolytic degradation, and a wetting agent comprising the composition.

Preferred embodiments are set forth in the subclaims 2 to 4 and 5 to 20.

The composition in accordance with the present invention can be used for a variety of hydrophilic coating systems, gels and material substrates. The variation in the additional components of the composition in accordance with the present invention allows further enhancement of the wetting agent performance in relation to solubility stability and coating stability.

In addition, the composition in accordance with the present invention is non-toxic, can be easily prepared and is radiation sterilizable. Furthermore, the composition can be used in a variety of different wetting agents, independently on the base solutions. Unexpectedly, the composition in accordance with the present invention prevents or retards the degradation of a functional coating on a medical device from reactive species formed during exposure to radiation, even at an irradiation energy of up to 50 kGy.

When a medical device with a functional coating is sterilized by irradiation, highly reactive intermediates may be formed from water, e.g. •OH, $H_2O^+$, superoxide ($HO_2/O_2^-$), $H_2O_2$. These reactive moieties may cause reactions that are detrimental to the coating of the medical device. The composition of the present invention is more reactive towards a reactive moiety formed from water due to the irradiation, than the coating. The composition in accordance with the present invention may be furthermore able to inactivate a radical which may be formed in a polymer in the coating and thereby preventing uncontrolled and/or excessive crosslinking of the coating, and/or chain scission of the coating polymer, and/or delamination from the substrate.

The composition in accordance with the present invention is formulated to act as a highly protective agent for all types of functional coating systems subjected to high radiation levels when the coating substrate, i.e. the medical device, is subjected or exposed in a wetted environment comprising the composition. Further, since the composition in accordance with the present invention acts as protective agent, the functional coating of the medical device can be formed by crosslinking via an UV initiator, heat, γ-ray, X-ray or E-beam. The composition of the present invention is not limited to a particular coating material type or curing system, but can be used for any functional coating.

In addition, the composition in accordance with the present invention also acts as highly protective agent for hydrolytic degradation, in particular long term hydrolytic degradation. The wetting agent in accordance with the present invention is particularly suitable for protecting a gel like low delicate (hydrated) interpenetrating polymer network from irradiation and also provides hydrolytic stability.

The present invention provides a composition and a wetting agent comprising the composition which is mobile and in a liquid state, preferably the wetting agent is an aqueous wetting agent containing fully dissolved gallic acid or an ester, amide or oxadiazole derivative of gallic acid and/or CMC or a salt thereof and provides intimate contact with free moving hydrophilic polymer chains of the coating of a medical device. The composition in accordance with the present invention is mobile and free flowing at the surface of the coating.

The composition of the present invention allows preventing or retarding degradation of a functional coating from both, irradiation and hydrolytic degradation. In particular, the composition and the wetting agent of the present invention is capable of protecting even polymers such as gel networks, e.g. lightly crosslinked gel networks, and hydrophilic coatings, while in an aqueous environment and under extreme irradiation conditions. The composition and the wetting agent of the present invention further provide hydrolytic stability during the intended shelf-life of a wetted coated product.

The term "functional coating" includes hydrophilic coatings, antithrombogenic coatings, gel coatings, hydrophilic polymer coatings, polyvinylalcohol coatings, coatings for contact lenses, coatings based on water soluble polymers used especially in drug delivery systems, such as hydrogels, cellulose ethers, povidone, polyethylene glycol, polyacrylamides, polyacrylic acid copolymers, Polylactide-co-Glycolide (PGLA) and derivatives thereof. In a preferred embodiment in combination with any of the above or below embodiments, the functional coating is a hydrophilic coating.

In a first alternative, the composition for preventing or retarding degradation of a functional coating on a medical device comprises an antioxidant selected from gallic acid or a derivative thereof.

Gallic acid is a benzoic acid having the following structure:

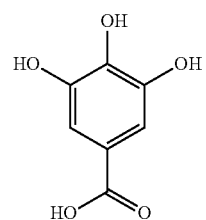

The IUPAC name is: 3,4,5-trihydroxybenzoic acid.

The derivative of gallic acid is an ester, amide or oxadiazole derivative of gallic acid.

The term "ester derivative of gallic acid" refers to an ester reaction product of an alcohol and gallic acid. The term "amide derivative of gallic acid" refers to the reaction product of an amine and gallic acid. The term "oxadiazole derivative of gallic acid" refers to the reaction product of oxadiazole and gallic acid.

In a preferred embodiment in combination with any of the above or below embodiments, in the composition in accordance with the present invention, the ester derivative of gallic acid is a reaction product of gallic acid and an aliphatic C1 to C16 alcohol, more preferably a reaction product of gallic acid and an aliphatic C1 to C12 alcohol. Most preferably, the ester derivative of gallic acid is selected from propyl gallate, methyl gallate, ethyl gallate, octyl gallate and lauryl gallate or mixtures thereof, in particular, the ester derivative of gallic acid is propyl gallate.

The term "aliphatic alcohol" refers to a saturated linear or branched alcohol.

Propyl gallate is the reaction product of gallic acid and propanol and has the following structure:

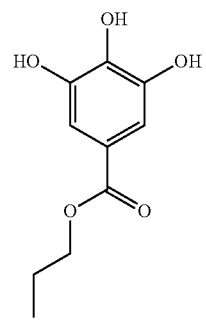

Other commonly used names are: n-propyl gallate, propyl 3,4,5-trihydroxybenzoate, gallic acid propyl ester, 3,4,5-trihydroxybenzoic acid propyl ester, 3,4,5-trihydroxybenzene-1-propylcarboxylate, CAS No 121-79-9.

In a preferred embodiment in combination with any of the above or below embodiments, in the composition in accordance with the present invention, the amide derivative of gallic acid is selected from gallic N,N-dimethylamide, gallic naphtylamide or mixtures thereof.

The oxadiazole derivative of gallic acid has the following structure:

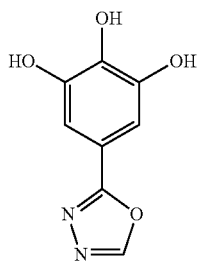

In a preferred embodiment in combination with any of the above or below embodiments, in the first alternative, the composition in accordance with the present invention, gallic acid or a derivative thereof is present in an amount of 0.001 to 5% by weight, more preferably 0.01 to 2% by weight, most preferably 0.05 to 0.5% by weight, in particular 0.1 to 0.2% by weight, based on the total weight of the composition.

In a second alternative, the composition of the present invention comprises carboxymethyl cellulose or a derivative or salt thereof.

Carboxymethyl cellulose (CMC) is a cellulose derivative, wherein some of the hydroxyl groups of the glucopyranose monomers that form the cellulose backbone are replaced with carboxymethyl groups (—$CH_2$—COOH). It is often used as its sodium salt, sodium carboxymethyl cellulose.

Carboxymethyl cellulose has the following structure:

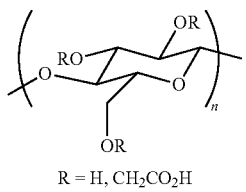

R = H, $CH_2CO_2H$

In a preferred embodiment in combination with any of the above or below embodiments, in the second alternative, the composition comprises a salt of carboxymethyl cellulose, more preferably the sodium salt of carboxymethyl cellulose. In sodium carboxymethyl cellulose R of the above structural formula is $CH_2CO_2Na$. Other commonly used names are sodium cellulose glycolate, Na-CMC, cellulose gum, sodium CMC, CAS No 9004-32-4.

The chemical formula of sodium CMC is $[C_6H_7O_2(OH)_x(OCH_2COONa)_y]_n$, where n is the degree of polymerization; x is 1.50 to 2.80; y is 0.2 to 1.50; x+y is 3.0 (y=degree of substitution).

In a further preferred embodiment of the second alternative in combination with any of the above or below embodiments, carboxymethyl cellulose or a derivative or salt thereof is present in an amount of 0.1 to 10% by weight, more preferably 0.2 to 7% by weight, particularly preferably 0.2 to 5% by weight, in particular 1 to 5% by weight, based on the total weight of the composition. Preferably, carboxymethyl cellulose is present as the sodium salt, i.e. Na-CMC.

In another preferred embodiment in combination with any of the above or below embodiments, the composition of the second alternative further comprises gallic acid or a derivative thereof, more preferably propyl gallate. Gallic acid derivates are as described above.

In a preferred embodiment in combination with any of the above or below embodiments, in the composition in accordance with the present invention of the second alternative, gallic acid or a derivative thereof is present in an amount of 0.001 to 1% by weight, more preferably 0.01 to 0.5% by weight, in particular 0.02 to 0.2% by weight, based on the total weight of the composition.

In a preferred embodiment in combination with any of the above or below embodiments, the composition in accordance with the present invention further comprises an aqueous or oil based base solution or a lipid media or a combination thereof.

The term "aqueous solution" refers to any solution wherein water is the main component, i.e. is present in at least 50% by weight, base on the total weight of the aqueous solution.

The term "oil based solution" refers to a solution comprising one or more oils. Preferably, the oil based solution comprises polyethylene glycol, propylene glycol, glycerol and/or polyvinyl alcohol. Essential oils may be included in up to 0.5% by weight, based on the oil based solution. If an oil based solution is used, the oil based solution may be present in an amount of up to 49.8% by weight, based on the total composition.

In a preferred embodiment in combination with any of the above or below embodiments, the aqueous base solution is selected from distilled water, deionized water, reverse osmosis water, filtered water or a saline solution. More preferably, the aqueous base solution is a saline solution, in particular a saline solution having physiological osmolarity.

In a further preferred embodiment in combination with any of the above or below embodiments, the aqueous base solution is present in an amount of 50 to 99.99% by weight, more preferably 85 to 99.8% by weight, in particular 85 to 94% by weight, based on the total weight of the composition.

In a further preferred embodiment in combination with any of the above or below embodiments, the aqueous base solution is a saline solution having physiological osmolarity and is present in an amount of 85 to 94% by weight, based on the total weight of the composition.

In a preferred embodiment in combination with any of the above or below embodiments, the composition in accordance with the present invention is present as a suspension within and/or around the functional coating. The term "around" as used herein has the meaning of "in the vicinity" of the coating.

In a further preferred embodiment in combination with any of the above or below embodiments, the composition of the present invention of the first alternative further comprises a stabilizer and/or a buffer solution.

In a preferred embodiment in combination with any of the above or below embodiments, the composition of the present invention of the second alternative further comprises a stabilizer, a solution enhancer and/or a buffer solution.

In another preferred embodiment in combination with any of the above or below embodiments, the stabilizer is selected from polylactams, such as polyvinylpyrrolidone (PVP), polyurethanes, homo- and copolymers of acrylic and methacrylic acid, polyvinyl alcohols, polyvinylethers, maleic anhydride based copolymers, polyesters, such as polylactides, polyglycolides, polycaprolactones, and polynucleotides, vinylamines, polyethyleneimines, polyethyleneoxides, polycarboxylic acids, polyamides, polyanhydrides, polyphosphazenes, cellulosics, such as methyl cellulose, carboxymethyl cellulose, hydroxymethylcellulose, hydroxyxpropylcellulose and other polysaccharides, such as chitosans, hyaluronic acids, alginates, gelatins, chitins, heparins, and dextrans, polypeptides/proteins, such as collagens, fibrins, elastins, and albumin. Of these, PVP is particularly preferred.

In a further preferred embodiment in combination with any of the above or below embodiments, PVP is present in the composition of the present invention in an amount of 0.1 to 40% by weight, more preferably 3 to 20% by weight, most preferably 4 to 12% by weight, and in particular 7 to 12% by weight, based on the total weight of the composition.

As gallic acid and derivatives thereof have a limited solubility in water, a solution enhancer may be added to the composition in accordance with the present invention. In a preferred embodiment in combination with any of the above or below embodiments, the solution enhancer is selected from a polyol, more preferably ethylene glycol, diethylene glycol, propylene glycol, glycerol, in particular propylene glycol.

Under certain conditions and concentrations the carboxymethyl cellulose or salt thereof and/or the esters of gallic acid may recrystallize out of the solution over time. When a stabilizer, in particular in the above-mentioned concentrations, is added, no recrystallization occurs and homogeneity of the solution is maintained.

In a further preferred embodiment in combination with any of the above or below embodiments, the solution enhancer, preferably propylene glycol, is present in the composition of the present invention in an amount of 0.1 to 49.8% by weight, more preferably 1 to 20% by weight, in particular 2 to 10% by weight, based on the total weight of the composition.

As indicated above, the esters of gallic acid have limited solubility in water, e.g. the solubility of propyl gallate is 3.5 mg/mL. Furthermore, the dissolution rates are slow at room temperature. When adding a polyol, such as propylene glycol, the dissolution rate significantly increases without the necessity of heat. In a preferred embodiment in combination with any of the above or below embodiments, the weight ratio of water or saline solution to propylene glycol is 1.0 to 0.3 to 1.0 to 1.3, preferably 1.0:0.7.

If a wetting agent is heated to 45° C. and greater, the miscibility of propyl gallate increases. However, after cooling propyl gallate can precipitate out of the solution to form low order structure entities that resemble needle lattice structures. The addition of propylene glycol prevents or eliminates the necessity of elevating the temperature of the solution. Adding a component to a solution at elevated temperature can generate a super-saturated solution, i.e. the solution contains more of the dissolved component than under normal room temperature conditions. On cooling a super-saturated solution, the dissolved component can precipitate out of the solution. With the addition of propylene glycol, elevation of the temperature is no longer required as it increases the dissolvability of the solution for that component. The addition of propylene glycol therefore permits dissolving of gallic acid or a derivative thereof at low and ambient temperatures.

In the case where glycerol is employed, it may be necessary to add some heat to the solution in order to achieve full dissolution of the propyl gallate. Further, the sequence of the mixing steps and its effect on the relative dissolution of propyl gallate when all component concentrations and temperature are kept constant, is as follows:

Addition of propylene glycol to propyl gallate, then addition of saline or distilled water: fast reaction (high rate of dissolution of propyl gallate);

Addition of saline/distilled water to propyl gallate, then addition of propylene glycol: slow reaction (low rate of dissolution of propyl gallate);

Addition of propylene glycol to saline/distilled water, then addition of propyl gallate: fast reaction (high rate of dissolution of propyl gallate);

Employing glycerol instead of propylene glycol: slow reaction (low rate of dissolution of propyl gallate).

The polyol, e.g. propylene glycol, further functions as antimicrobial and antifungal agent and therefore delivers antimicrobial and antifungal properties to the composition in accordance with the present invention.

In another preferred embodiment in combination with any of the above or below embodiments, the buffer solution has a pH of 2.0 to 7.4, more preferably 3.0 to 6.5, in particular 3.0 to 4.0. The buffer solution is added to generate solution stability with regard to pH and prevent the esters of gallic acid from recrystallization. Suitable buffers include monocarboxylic acids, such as formic acid, acetic acid, propionic acid, 3-hydroxypropionic acid, 2,3-dihydroxypropionic acid, gluconic acid, benzoic acid, cinnamic acid, lactic acid, mandelic acid, glycolic acid, phenylacetic acid, chlorobenzoic acid, naphtoic acid, toluic acid, N-acetylglycine; dicarboxylic acids, such as oxalic acid, malonic acid, succinic acid, glutaric acid, adipic acid, phthalic acid, isophthalic acid, terephthalic acid, malic acid, tartaric acid, itaconic acid, and fumaric acid; tri- and tetracarboxylic acids, such as citric acid and 1,2,3,4-butanetetracarboxylic acid; amino acids, such as tryptophan, aspartic acid, glutamic acid, aminobenzoic acid, glycylglycine, glycylglycylglycine, glutathione, N-phenylglycine, carnosine, niacin; aminosulfonic acids; and inorganic acids, such as hydrofluoric acid, cyanic acid and nitrous acid.

In a preferred embodiment in combination with any of the above or below embodiments, the composition in accordance with the present invention comprises 0.01 to 2% by weight of propyl gallate, 0.1 to 40% by weight of PVP, and 0.1 to 49.8% by weight of propylene glycol; more preferably 0.05 to 0.5% by weight of propyl gallate, 3 to 20% by weight of PVP, and 1 to 20% by weight of propylene glycol; in particular 0.1 to 0.2% by weight of propyl gallate, 4 to 12% by weight of PVP, and 2 to 10% by weight of propylene glycol. Particularly preferable is a composition comprising 0.1 to 0.2% by weight of propyl gallate, 4 to 12% by weight of PVP, and 2 to 10% by weight of propylene glycol and a buffer having a pH of 4 to 5.

In another preferred embodiment in combination with any of the above or below embodiments, the composition in accordance with the present invention comprises 0.1 to 10% by weight of sodium carboxymethyl cellulose, 0 to 1% by weight of propyl gallate, and 1 to 20% by weight of propylene glycol; more preferably 0.2 to 7% by weight of sodium carboxymethyl cellulose, 0.01 to 1% by weight of propyl gallate, and 1 to 15% by weight of propylene glycol; in particular 0.2 to 5% by weight of sodium carboxymethyl cellulose, 0.02 to 0.2% by weight of propyl gallate, and 2 to 10% by weight of propylene glycol, based on the total weight of the composition. Particularly preferable is a composition comprising 0.2 to 2% by weight of sodium carboxymethyl cellulose, 0.02 to 0.2% by weight of propyl gallate, and 2 to 10% by weight of propylene glycol, based on the total weight of the composition, and a buffer having a pH of 4 to 5. Alternatively, particularly preferable is an embodiment composition comprising 2 to 5% by weight of sodium carboxymethyl cellulose, 0% by weight of propyl gallate, and 2 to 10% by weight of propylene glycol, based on the total weight of the composition, and a buffer having a pH of 4 to 5.

In a further preferred embodiment in combination with any of the above or below embodiments, the composition in accordance with the present invention further comprises an antibacterial agent, such as a silver salt, an acceptable iodine source such as povidone iodine, chlorhexidine salts such as the gluconate, actetate, hydrochloride or quaternary antibacterial agents such as benzalkonium chloride or other antiseptics or antibiotics. The presence of antibacterial agents reduces the risk of infection. The composition in accordance with the present invention may further comprise an osmolarity increasing agent such as urea, sodium chloride and/or any salt or organic low molecular weight compound being physiological acceptable and non-irritating for adjusting the ion strength of the coating approximately to the physiological range, the coating preferably being isotonic in use. The composition in accordance with the present invention may also comprise preservatives and pharmaceuticals, such as antimicrobial agents and antithrombogenic agents, or plasticizers.

The medical device having a functional coating may be any device that should be able to move against body tissue, such as an inner wall of a body vessel or the outer surface of the eye. Preferably, the medical device is a medical tubing, guidewire, canula, stent, stent graft, anastomotic connector, synthetic patch, lead electrode, needle, senor, surgical instrument, angioplastic balloon, wound drain, shunt, tubing, infusion sleeve, urethal insert, pellet, implant, blood oxygenator, pump, vascular graft, vascular access port, heart valve, annuloplasty ring, suture, surgical clip, surgical staple, pacemaker, implantable defibrillator, neurostimulator, orthopedic device, cerebrospinal fluid shunt, implantable drug pump, spinal cage, artificial disc, replacement device for nucleus pulposus, ear tube, intraocular lens, tubing used in minimally invasive surgery, catheter, such as an intraluminal catheter, e.g. a urinary or cardiovascular catheter. Preferably, the medical device may be packed together with the composition in accordance with the present invention, more preferably the medical device is contacted with the composition or the wetting agent of the present invention, is sterilized and is stored in the wetting agent as a ready-to-use assembly. In such a ready-to-use assembly, the medical device can be used directly after opening of the packaging.

The wetting is achieved by contacting the medical device and the composition or the wetting agent in accordance with the present invention. Contacting may be achieved by dipping, spraying, vaporizing the composition or the wetting agent and contacting the device with the vaporized composition or wetting agent.

The composition in accordance with the present invention is able to prevent or retard degradation of functional coatings on a medical device. The composition of the present invention can be easily prepared from non-toxic components and can be used for radiation sterilization. When used for sterilizing a medical device no degradation of the functional coating on the medical device from reactive species generated during exposure of radiation occurs in the presence of the composition of the present invention.

Further, the composition in accordance with the present invention is also able to prevent or retard hydrolytic degradation and is particularly suitable for wetted environments.

The following examples further describe the present invention.

EXAMPLES

General Procedure for the Preparation of the Propyl Gallate Solutions:

Propyl Gallate is only slightly soluble in water, but with the addition of propylene glycol the solubility of propyl gallate increases. Propylene glycol has a great affinity to water and also is a viable alternative additive to glycerol from a costing perspective.

1. Using a standard disposable pipette, 5 g of propylene glycol or glycerol was placed in a 200 ml glass beaker.
2. 10 g of 0.9 wt % saline (9 g/L sodium chloride solution) was then added to the propylene glycol or glycerol.
3. 0.01 to 0.5 g of propyl gallate is added to the beaker and distilled water or 0.9 wt % saline (9 g/L sodium chloride solution) was added to amount to 100 ml of solution.
4. Taking the beaker by hand, the contents was gently swirled for about 2 minutes to promote mixing, resulting with the propyl gallate being visibly dissolved. This premixing ratio of saline or water with propylene glycol or glycerol delivers a method whereby heating of the beaker is not required to achieve complete dissolution of the propyl gallate. However, in the case where glycerol is employed, it may be necessary to add some heat to the solution in order to achieve full dissolution of the propyl gallate. While the addition of glycerol to distilled water/water/saline increases the degree of dissolution and dissolution rate of propyl gallate, it is significantly less effective than propylene glycol. For that reason, it may be necessary to add heat when using glycerol, especially where relatively high concentration of propyl gallate is being considered (i.e. 0.15 to 0.5 wt % propyl gallate).
5. Other additives such as polyvinylpyrrolidone (PVP; Sigma Aldrich; K60, 45% in $H_2O$), surfactants such as Tween 20 and 80 (non-ionic agent supplied by Sigma Aldrich), buffer solutions (pH 4.00 (20° C.); citric acid/sodium hydroxide/hydrogen chloride supplied by Merck Chemicals KGaA), may optionally be added after mixing of the propyl gallate has been accomplished.
6. A magnetic stirrer bar was placed in the beaker and the beaker placed on a magnetic stirrer (IKA RT5 Magnetic Stirrer). The heat settings are set at zero and the rotation speed set between the 3 and 4 mark on the stirrer equipment. The contents are stirred slowly for an hour to ensure a homogenous solution.

The amounts of the components are shown in Tables 1 to 5 below.

General Procedure for the Preparation of the CMC Solutions:

Preparation of Sodium Carboxylmethyl Cellulose (Na-CMC) Pre-Mix:

1. 100 g of deionized water was weighed and poured into a glass beaker.
2. The required amount of Na-CMC as specified by Tables 6 and 7 was weighed.
3. The water was placed on a magnetic stirrer and the stirrer set to 80° C. to promote the dispersion and dissolution of the Na-CMC powder.
4. The Na-CMC was slowly added over 2-3 hour period until dissolved into the water (the mixing time may greatly reduce depending on the amount of CMC required).

5. The mixture was allowed to cool to room temperature while stirring of the solution was maintained.

6. When the mixture has cooled, 5 g of buffer (pH 4) was added and stirring was continued for 15-30 minutes.

Preparation of Wetting Agent Pre-Mix:

1. The correct amount of propyl gallate in accordance with Tables 6 and 7 was weighed and placed into a 100 mL glass beaker.

2. 5 g of polypropylene glycol was added to the glass beaker containing the propyl gallate.

3. In short succession, 9.5 mL of saline solution was added to the glass beaker containing the mixture of propyl gallate and polypropylene glycol.

4. The glass beaker and its contents was stirred by hand for 2 minutes until all the propyl gallate has visually dissolved in the liquid mixture.

5. Where specified in Table 6 for ultrasonic agitation of the mixture, immediately after adding the 9.5 mL of saline fluid to the propyl gallate and polypropylene glycol mixture, this 100 mL glass beaker (containing all ingredients) was placed into an ultrasonic bath for 30 seconds.

Combining Pre-Mixes:

1. Wetting Agent Premix was added into the CMC Premix

2. The contents were stirred employing a magnetic stirrer with no heat

3. Stirring was permitted for 2 hours.

Other additives such as Tween 20 and 80 (non-ionic agent supplied by Sigma Aldrich), buffer solutions (pH 4.00 (20° C.); citric acid/sodium hydroxide/hydrogen chloride supplied by Merck Chemicals KGaA), may optionally be added after mixing of the Na-CMC and/or propyl gallate has been accomplished.

General Procedure for the Preparation of the Test Specimen:

Extruded polymer shafts reflecting a diameter of 4.5 mm with an ID of 3.0 mm were selected for the testing. These shafts had been dipped and cured resulting with a uniform hydrophilic coating along the polymeric tube substrate. It is important to ensure that the same processing parameters of dipping and UV curing of the coating was maintained so as to eliminate any variability in coating integrity. The shaft material used for these series of trials was polyurethane block copolymers and plasticized polyvinyl chloride. The shafts were placed on a cutting matt and with a sharp blade; the polymeric coated tubes were cut to a length of approximately 200 mm. The distal end of the shaft was cut at an angle to distinguish the distal end form the proximal end (at the distal end, the coating tends to be slightly thicker and the angle cut provides information for the friction test operator). For all specimens prepared for friction testing, latex gloves were worn during all handling and cutting steps to prevent contamination of the surfaces of specimen substrates.

Friction Testing (Coefficient of Friction—COF):

1. The protocol test program option was selected to access the test parameters

2. The following information was inputted into the program:
   a. Clamp force=300 g
   b. Test Speed=180 mm/minute
   c. Test distance=60 mm.
   d. Repeated Friction Test Cycles=25
   e. Speed=3 cm/s 3. A stainless steel mandrel of appropriate diameter to the inner lumen of the coated test specimen was inserted fully into the test specimen. The tube was positioned such that a clamp was placed on the section that had a clean level cut (the angled tube cut faced towards the water container of the friction testing machine).

4. The clamping pads were of 60 DURO supplied by Harland; (Part Number 102149).

5. This test assembly was mounted onto the Harland Friction Tester FTS 5000 after it had been calibrated.

6. A container was filled with water to a predetermined mark so that the coated test specimen and clamps were submerged prior to testing. The clamp section of the specimen remained out of the water while the angled cut end of the specimen was submerged in the water.

7. The test was started after 30 seconds had elapsed to ensure that the coating was fully hydrated.

8. The force expressed into the clamps was automatically recorded in the form of a graph of gram force versus time.

9. After the test was completed, a reading of average gram force and maximum gram force was presented by the instrument.

10. The COF was calculated by dividing the average gram force reading by 300 grams 11. After each test, a wetted cloth was used to remove any residual coating that may have accumulated on the pads.

ABBREVIATIONS

PG=propyl gallate; supplied by Sigma Aldrich in the form of powder
Na-CMC=sodium carboxymethyl cellulose
PPG=propylene glycol
DW=distilled water
Buffer:
HPCE grade buffer solution with a pH value of 4.0 at 25° C. with a concentration of 20 mM sodium citrate (supplied by Sigma Aldrich).

Results

Example 1: Propyl Gallate Solutions a) Effects of Glycerol on Coating Integrity

TABLE 1

| Dosage (kGy) | PG (wt %) | PVP (wt %) | PPG (wt %) | pH Buffer (wt %) | Carrier Solution | Glycerol (wt %) | COF (Number of Friction Cycles; 300 g clamp force) | | | | |
|---|---|---|---|---|---|---|---|---|---|---|---|
| | | | | | | | 0 | 5 | 10 | 20 | 25 |
| 45 | 0.2 | 5 | 0 | 0 | DW | 5 | 4.2 | 4.1 | 4.1 | 4.1 | 4.1 |
| 45 | 0.2 | 5 | 0 | 0 | DW | 0 | 4.5 | 4.3 | 4.3 | 4.3 | 4.3 | b) Effects of PG Concentration on Coating Integrity

TABLE 2

| Dosage (kGy) | PG (wt %) | PVP (wt %) | PPG (wt %) | pH Buffer (wt %) | Carrier Solution | Glycerol (wt %) | COF (Number of Friction Cycles; 300 g clamp force) | | | | |
|---|---|---|---|---|---|---|---|---|---|---|---|
| | | | | | | | 0 | 5 | 10 | 20 | 25 |
| 45 | 0   | 10 | 0 | 0 | DW | 5 | 30  | 90  | 120 | 160 | 190 |
| 45 | 0.2 | 10 | 0 | 0 | DW | 5 | 4   | 4.3 | 4.2 | 4.2 | 4.3 |
| 45 | 0.5 | 10 | 0 | 0 | DW | 5 | 4   | 4.3 | 4.3 | 4.3 | 4.3 |
| 45 | 0.2 | 5  | 0 | 0 | DW | 5 | 4.3 | 4.1 | 4.1 | 4.1 | 4.1 | c) Effects of PG concentration on coating integrity

TABLE 3

| Dosage (kGy) | PG (wt %) | PVP (wt %) | PPG (wt %) | pH Buffer (wt %) | Carrier Solution | Glycerol (wt %) | COF (Number of Friction Cycles; 300 g clamp force) | | | | |
|---|---|---|---|---|---|---|---|---|---|---|---|
| | | | | | | | 0 | 5 | 10 | 20 | 25 |
| 45 | 0   | 5 | 0 | 0 | DW | 0 | 30  | 70  | 130 | 170 | 220 |
| 45 | 0.2 | 5 | 0 | 0 | DW | 0 | 4.2 | 4.1 | 4.1 | 4.1 | 4.1 | d) Effects of PPG concentration on coating integrity

TABLE 4

| Dosage (kGy) | PG (wt %) | PVP (wt %) | PPG (wt %) | pH Buffer (wt %) | Carrier Solution | Glycerol (wt %) | COF (Number of Friction Cycles; 300 g clamp force) | | | | |
|---|---|---|---|---|---|---|---|---|---|---|---|
| | | | | | | | 0 | 5 | 10 | 20 | 25 |
| 45 | 0.2 | 0 | 0 | 4 (10) | saline | 0 | 8.0 | 6.0 | 6.0 | 6.0 | 6.0 |
| 45 | 0.2 | 0 | 5 | 4 (10) | saline | 0 | 6.0 | 4.5 | 4.5 | 4.5 | 4.5 | e) Effects of carrier solution on coating integrity

TABLE 5

| Dosage (kGy) | PG (wt %) | PVP (wt %) | PPG (wt %) | pH Buffer (wt %) | Carrier Solution | Glycerol (wt %) | COF (Number of Friction Cycles; 300 g clamp force) | | | | |
|---|---|---|---|---|---|---|---|---|---|---|---|
| | | | | | | | 0 | 5 | 10 | 20 | 25 |
| 45 | 0.2 | 0 | 5 | 4 (10) | saline | 0 | 5.0 | 4.5 | 4.5 | 4.5 | 4.6 |
| 45 | 0.2 | 0 | 5 | 4 (10) | DW     | 0 | 7.0 | 7.0 | 6.5 | 6.5 | 6.5 |

As can be seen from the test results, in the absence of propyl gallate, the coefficient of friction (COF) is much higher than in the presence of propyl gallate. Furthermore, the COF increases with increase in the number of cycles. If propyl gallate is present, the COF is low and maintains almost constant (Table 2, Table 3).

Furthermore, the COF can be adjusted by adding further additives or by selecting the carrier solution and/or the pH.

Example 2: CMC Solutions

Formulations based on propyl gallate (PG) and sodium carboxymethyl cellulose (Na-CMC) were developed to further enhance the wetting agent performance. The samples were prepared with polypropylene glycol and buffer content maintained constant throughout the study to demonstrate the influence of the main stabilizing component ingredients, i.e. propyl gallate and sodium carboxymethyl cellulose.

The coating integrity and hydrolytic stability of the coating were tested after subjecting the hydrated specimens to 45 kGy gamma irradiation dosages. The primary objective of the wetting agent is to protect the hydrated hydrophilic coating during the sterilization cycles and secondarily, to provide hydrolytic stability to the coating, reflecting real-world shelf-life product indication.

The hydrolytic stability of the coating was assessed by interpreting the coating frictional stability performance over the 25 frictional cycles after subjecting coated hydrated specimens to accelerated aging for periods of 15 days (T15) and 30 days (T30), respectively, at an ageing temperatures of 50° C. All specimens were subjected to 45 kGy irradiation dosages. Time Zero (T0) directly after exposure captures the isolated effects of gamma irradiation on the coating integrity.

TABLE 6

Stability of wetting agent formulations after 45 kGy exposure

|  | Sample 1 | Sample 2 | Sample 3* | Sample 4 |
| --- | --- | --- | --- | --- |
| PG (wt %) | 0.02 | 0.20 | 0.02 | 0.10 |
| PPG (wt %) | 5.00 | 5.00 | 5.00 | 5.00 |
| Na-CMC (wt %) | 0.20 | 0 | 0.20 | 0.10 |
| Buffer (wt %) | 5.00 | 5.00 | 5.00 | 5.00 |
| T0 | Meta-stable | stable | stable | stable |
| T15 | Not stable | stable | stable | stable |
| T30 | Meta-stable | stable | stable | stable |

*= ultrasonic agitation;
T0 = directly after exposure;
T15 = after 15 days at 50° C.;
T30 = after 30 days at 50° C.

After 15 days ageing at 50° C. in a hydrated state after 45 kGy exposure, the data indicate that PG provides further stability within the formulation. When comparing Samples 1 and 3, the formulations are identical, but Sample 3 was ultrasonically agitated to promote the dissolution of the propyl gallate (PG) and enhances the efficacy of the PG within the solution and coating. Comparing Sample 3 to Sample 5, suggests that 0.1 wt % of PG and 0.1 wt % of CMC are sufficient to deliver coating stability after irradiation and ageing of the product specimens.

After 30 days ageing at 50° C. in a hydrated state after 45 kGy exposure, the data highlights:

PG at concentrations of 0.2 wt % provide adequate stability alone (Sample 2)

Ultrasonic agitation enhances the efficacy of PG dissolution (Samples 1 and 3)

A relative low 1:1 ratio of PG to Na-CMC delivers adequate coating stability (Sample 4).

Further developments were focused on increasing the percentage of Na-CMC within the formulation. The following results depict Na-CMC concentrations of 2 wt % and 5 wt % and assessing the influence of PG.

TABLE 7

Stability of wetting agent formulations after 45 kGy exposure

|  | Sample 5 | Sample 6 | Sample 7 | Sample 8 |
| --- | --- | --- | --- | --- |
| PG (wt %) | 0.20 | 0 | 0.02 | 0 |
| PPG (wt %) | 5.00 | 5.00 | 5.00 | 5.00 |
| Na-CMC (wt %) | 2.00 | 2.00 | 5.00 | 5.00 |
| Buffer (wt %) | 5.00 | 5.00 | 5.00 | 5.00 |
| T0 | stable | stable | stable | stable |
| T15 | stable | stable | stable | stable |
| T30 | stable | stable | stable | stable |

T0 = directly after exposure;
T15 = after 15 days at 50° C.;
T30 = after 30 days at 50° C.

At T0 after 45 kGy exposure, all formulations exhibited optimum coating friction and wear characteristics. After 15 days ageing at 50° C. in a hydrated state after 45 kGy exposure, all formulations exhibited optimum coating friction and wear characteristics. After 30 days ageing at 50° C. in a hydrated state after 45 kGy exposure, all formulations exhibited optimum coating friction and wear characteristics.

Na-CMC delivers excellent stability to the coating and can be used in conjunction with low concentration of PG to further improve the coating stability as indicated by results obtained in Tables 6 and 7.

The invention claimed is:

1. A wetting liquid formulation, comprising:
   a liquid comprising an aqueous or oil-based base solution, a lipid media, or a combination of both;
   an antioxidant dissolved in the liquid, the antioxidant being an oxadiazole derivative of gallic acid, and further comprising a solution enhancer to increase dissolvability of the antioxidant; and
   wherein wetting a medical device with the wetting liquid formulation reduces degradation of a functional coating on the medical device.

2. The wetting liquid formulation of claim 1, wherein the oxadiazole derivative of gallic acid is present in an amount of 0.001% to 5% by weight based on a total weight of the composition.

3. The wetting liquid formulation of claim 1, wherein the aqueous base solution is selected from a group consisting of distilled water, deionized water, reverse osmosis water, filtered water and a saline solution.

4. The wetting liquid formulation of claim 1, wherein the aqueous base solution is present in an amount of from 50% to 99.99% by weight, based on a total weight of the composition.

5. The wetting liquid formulation of claim 1, wherein the oxadiazole derivative of gallic acid is present as a suspension within and/or around the functional coating.

6. The wetting liquid formulation of claim 1, further comprising a stabilizer and/or a buffer solution.

7. The wetting liquid formulation of claim 3, wherein the solution enhancer is selected from ethylene glycol, diethylene glycol, propylene glycol, or glycerol, and is present in an amount of 0.1% to 49.8% by weight, based on the total weight of the composition.

8. The wetting liquid formulation of claim 6, wherein the buffer solution has a pH of from 2.0 to 7.4 and wherein the buffer solution prevents the gallic acid derivatives from recrystallization.

9. The wetting liquid formulation of claim 1, wherein the composition is free of polyvinyl alcohol.

10. The wetting liquid formulation of claim 1, further comprising polyvinylpyrrolidone (PVP) in an amount of 0.1 to 40% by weight.

* * * * *